United States Patent [19]

Clausen et al.

[11] Patent Number: 4,861,920

[45] Date of Patent: Aug. 29, 1989

[54] PROCESS FOR THE PREPARATION OF 2,6-DIHYDROXYNAPHTHALENE

[75] Inventors: Martin Clausen; Paul Rys, both of Zürich, Switzerland

[73] Assignee: Ciba-Geigy Corporation, Ardsley, N.Y.

[21] Appl. No.: 167,807

[22] Filed: Mar. 14, 1988

[30] Foreign Application Priority Data

Mar. 24, 1987 [CH] Switzerland ............... 1120/87

[51] Int. Cl.$^4$ .................. C07C 37/00; C07C 37/08
[52] U.S. Cl. ............................. 568/741; 568/735
[58] Field of Search ................... 568/735, 741, 768

[56] References Cited

U.S. PATENT DOCUMENTS

| | | | |
|---|---|---|---|
| 2,776,322 | 1/1957 | Webster et al. | 568/741 |
| 2,883,430 | 4/1959 | Jong | 568/741 |
| 3,141,046 | 7/1964 | Bichet et al. | 260/610 |
| 4,262,143 | 4/1981 | Becker et al. | 568/574 |
| 4,503,262 | 3/1985 | Gupton et al. | 568/741 |

FOREIGN PATENT DOCUMENTS

| | | | |
|---|---|---|---|
| 032758 | 7/1981 | European Pat. Off. | |
| 2517591 | 10/1975 | Fed. Rep. of Germany | 568/741 |
| 1277033 | 2/1961 | France | |
| 2238225 | 10/1987 | Japan | 568/735 |
| 1313360 | 4/1973 | United Kingdom | 568/768 |

Primary Examiner—Werren B. Lone
Attorney, Agent, or Firm—Kevin T. Mansfield; Edward McC. Roberts

[57] ABSTRACT

Process for the preparation of 2,6-dihyroxynaphthalene from 2,6-dialkylnaphthalenes, which are dissolved in an inert solvent and are oxidized at temperatures from 50° to 150° C. by means of oxygen or oxygen donors, in the presence of an alkali metal salt or alkaline earth metal salt of an organic carboxylic acid having 5 to 14 carbon atoms, to give the corresponding 2,6-dialkylnaphthalene dihydroperoxides, and the latter are subsequently hydrolysed.

The process results in pure, easily isolatable products in a good yield. The process products according to the invention are valuable intermediates for, inter alia, dyes, plastics, synthetic fibres, polymeric liquid crystals or pharmaceuticals.

15 Claims, No Drawings

PROCESS FOR THE PREPARATION OF 2,6-DIHYDROXYNAPHTHALENE

The present invention relates to a novel, improved process for the preparation of 2,6-dihydroxynaphthalene by the oxidation of corresponding 2,6-dialkylnaphthalenes and subsequent hydrolysis of the dihydroperoxides formed.

A process for the preparation of 2,6-diisoproylnaphthalene dihydroperoxide is already known from U.S.-A 4,503,262. The catalysts used are, for example, oxides or hydroxides of heavy metals or alternatively heavy metal salts of organic acids. The process is carried out at 50° to 100° C. using aliphatic hydrocarbons as solvents.

It has now been found that theoxidation of 2,6-dialkylnaphthalenes can also be carried out without the use of heavy metal catalysts and, indeed, more selectively and with good yields by using alkali metal salts or alkaline earth metal salts of organic carboxylic acids instead.

The present invention therefore relates to a process for the preparation of 2,6-dihydroxynaphthalene, which comprises oxidizing 2,6-dialkylnaphthalenes, dissolved in inert organic solvents, at temperatures from 50° to 150° C. by means of oxygen or oxygen donors in the presence of an alkali metal salt or alkaline earth metal salt of an organic carboxylic acid having 5 to 14 carbon atoms, to give the corresponding 2,6-dialkylnaphthalene dihydroperoxides,and then hydrolysing the latter.

The present invention also relates to the 2,6-dihydroxynaphthalenes prepared in accordance with the process and to their use as intermediates for the preparation of, for example, dyes, plastics, synthetic fibres, polymers with phases of mesomorphic state (liquid crystals) or pharmaceuticals.

The 2,6-dialkylnaphthalenes employed in accordance with the invention are those having lower alkyl substituents, having preferably 2 to 4, and especially 3 or 4, carbon atoms in the indicated positions of the naphthalene ring system.

Examples of such alkyl groups are ethyl, propyl, isopropyl, butyl, isobutyl, sec-butyl or tert-butyl, alkyl groups having a tertiary proton in the α-position relative to the aryl system, in particular isopropyl or sec-butyl, being preferred.

The alkali metal salts or alkaline earth metal salts of organic carboxylic acids having 5 to 14 carbon atoms used in the process according to the invention are preferably compounds of the formula

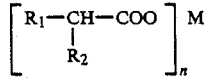

in which $R_1$ is $C_1$–$C_{12}$alkyl or naphthyl and $R_2$ is hydrogen or $C_1$–$C_9$-alkyl, the sum of the carbon atoms in the substituents $R_1$ and $R_2$ is 3 to 12, M is lithium, especially sodium and potassium, and also magnesium, strontium, barium and, in particular, calcium and n is 1 or 2, depending on the valency of the metals M.

The following are examples of suitable organic carboxylic acids whose salts are used: n-valeric acid, caproic acid, n-heptanoic acid, caprylic acid, pelargonic acid, capric acid, lauric acid, myristic acid, 2-ethylbutyric acid, 4-ethylhexanoic acid, 3-ethylheptanoic acid, 2-naphthylacetic acid and, preferably, 2-ethylcaproic acid.

The formation of salts can also take place in situ, i.e. the organic carboxylic acids and, as a rule, alkali metal hydroxides or alkaline earth metal hydroxides are added separately to the reaction mixture.

It is preferable to use the calcium salts, and particularly the sodium salts or potassium salts, of these acids, specifically in amounts of 0.1 to 0.5% by weight, relative to the weight of the 2,6-dialkylnaphthalenes.

If appropriate, it is also possible to employ additionally so-called reaction initiators, for example organic free-radical formers belonging to the group comprising peroxides for example di-tert-butyl peroxide, or comprising azo compounds, for example azobisisobutyronitrile, for the oxidation reaction according to the invention. The monoperoxides or dihydroperoxides formed in the oxidation (for example 2,6-diisopropylnaphthalene dihydroperoxide), for example those from a previous oxidation, can also be used as so-called reaction initiators.

The amounts of these initiators are about 0.1 to 0.5% by weight, relative to the weight of the 2,6-dialkylnaphthalenes.

The oxidation is carried out in an inert organic solvent, aromatic (benzene and halogenated benzenes) and, preferably, aliphatic hydrocarbons (heptane, octane or petroleum ether) being very suitable, particularly those having boiling ranges from 60° to 150° C.

The actual oxidizing agent used in the process according to the invention can be molecular oxygen or alternatively gases containing oxygen, for example air, or compounds which split off oxygen, for example ozone.

If oxygen is used as the oxidizing agent, 0.1 to 1 m³, preferably 0.3 to 0.6 m³, of this gas per kg of the 2,6-dialkylnaphthalenes and per hour is, for example, passed through the reaction mixture.

The reaction times are approximately within the range from 1 to 24 hours. The reaction temperatures are preferably within the range from about (70°–80°) to 130° C., the upper limit being set by the boiling point of the inert solvent used. The temperature range which is very particularly preferred is 80° to 110° C.

When the oxidation reaction is complete, the reaction mixture is slowly cooled to room temperature. The finely crystalline precipitate thereby deposited, containing essentially 2,6-dialkylnaphthalene dihydroperoxide and monohydroperoxide (a substantially single-substance dihydroperoxide can be obtained by recrystallizing the precipitate from an inert solvent), is separated off, taken up in a polar solvent, for example methanol, and subjected to hydrolysis, for example by mineral acids, such as hydrochloric acid or sulfuric acid. This is effected by heating the methanolic solution with stirring at temperatures from 40° to 65° C. for a short time (10 to 40 minutes).

If appropriate, the hydrolysis can also be carried out by means of acid solid catalysts, in particular acid ion exchangers. Methanol is then removed and a non-polar solvent (for example hexane, heptane or petroleum ether) is added to the residue, and the mixture is heated to approx. 60° C. The undissolved fractions are then removed, washed with an inert solvent (petroleum ether) and finally dried. This product is the process product according to the invention—2,6-dihydroxynaphthalene—and is obtained in very good yields (virtually quantitative)—relative to the 2,6-dialkylnaphthalene dihydroperoxide formed as an intermediate—and in a state of very high purity.

The filtrate (1) obtained after the finely crystalline precipitate has been removed (before the hydrolysis) contains essentially the starting compound and 2,6-dialkylnaphthalene monohydroperoxide. Filtrate (1) can be employed in a new oxidation reaction.

Any 2-hydroxy-6-alkylnaphthalene which may still be present crystallizes, on cooling, from the filtrate (2) obtained after the removal of the 2,6-dihydroxynaphthalene, and is also separated off and dried.

The process according to the invention can be carried out in a cyclic manner and hence also continuously.

Customary analytical methods, for example gas chromatography (GC) and particularly high-pressure liquid chromatography (HPLC) are used to monitor the process according to the invention and to analyse the products obtained.

The advantages of the process according to the invention are, on the one hand, the avoidance of heavy metal catalysts and, on the other hand, the easy removal of the dihydroperoxides obtained from the 2,6-dialkylnaphthalenes employed as starting compounds, and also from the monohydroperoxides of the said starting compounds which are formed as intermediates.

As mentioned, the process according to the invention can also be carried out continuously.

The products of the process are obtained in a good yield and purity. They are intermediates suitable for the preparation of a large number of chemical products, for example dyes, plastics, synthetic fibres, polymers with phases of mesomorphic state (liquid crystals) or pharmaceuticals.

The following examples illustrate the process according to the invention, but without limiting it to these examples. Unless otherwise stated, parts and percentages are by weight. The temperature is quoted in degrees Centigrade.

EXAMPLE 1

10 g of 2,6-diisopropylnaphthalene (purity 98% as analysed by gas chromatography (GC)), dissolved in 20 ml of n-heptane, are heated to 80° C. in a 100 ml four-necked flask equipped with a stirrer, a thermometer, a reflux condenser and a gas inlet frit. First 0.1 ml of a solution composed of 4 parts of 2-ethylcaproic acid, 2 parts of sodium hydroxide and 5 parts of water and then 0.02 g of α,α'-azobisisobutyronitrile are introduced into the solution with vigorous stirring and, finally oxygen is passed in a rate of 80 ml/minute for 24 hours.

Analysis of the resulting reaction product by HPLC indicates, in addition to unchanged starting material (2,6-diisopropylnaphthalene), oxidation products consisting of 91% by weight of the corresponding hydroperoxides (2,6-diisopropylnaphthalene monohydroperoxide and 2,6-diisopropylnaphthalene dihydroperoxide). The ratio by weight of monohydroperoxide to dihydroperoxide is about 6:1.

By cooling the reaction mixture to room temperature a crystalline precipitate consisting essentially of 2,6-diisoproylnaphthalene dihydroperoxide is obtained.

This precipitate is removed by filtration (see Example 2 for processing of the filtrate) and then 40 ml of methanol are added to the crystalline dihydroperoxide at room temperature, and 1 ml of concentrated (37% strength) hydrochloric acid is added dropwise and the solution is then heated to 60° C. and kept at this temperature for 15 minutes. After this time peroxides are no longer detected in the reaction solution (detection by means of HPLC).

The solution is concentrated by removing the methanol, and the residue is taken up in 50 ml of benzene, and the resulting solvent/product mixture is heated to 60° C.

The undissolved fractions in this mixture are removed, washed with cold water and petroleum ether (boiling range 110°–140° C.) and dried. This gives 0.42 g of 2,6-dihydroxynaphthalene (purity of 97% according to HPLC), which corresponds to a yield of 96%, relative to the 2,6-diisopropylnaphthalene dihydroperoxide obtained in the oxidation stage.

n-Valeric, capric, lauric or myristic acid can also be employed analogously and with comparable results instead of 2-ethylcaproic acid; potassium hydroxide can also be used instead of sodium hydroxide.

EXAMPLE 2

The filtrate obtained after removing the 2,6-diisopropylnaphthalene dihydroperoxide from the reaction product in Example 1, which contains 53% of 2,6-diisopropylnaphthalene and 41.5% of 2,6-diisopropylnaphthalene monohydroperoxide, is heated to 80° C. in the apparatus described in Example 1, and 0.1 ml of a solution composed of 4 parts of 2-ethylcaproic acid, 2 parts of sodium hydroxide and 5 parts of water is added. Oxygen is then passed into this reaction solution, with stirring, at a rate of 55 ml/minute. After a reaction time of 15 hours, the reaction solution contains (according to HPLC) the following main components: 30.5% of 2,6-diisopropylnaphthalene, 46% of 2,6-diisopropylnaphthalene monohydroperoxide and 10.5% of 2,6-diisopropylnaphthalene dihydroperoxide.

The oxidation products consist of the monohydroperoxides and dihydroperoxides mentioned to the extent of about 81% by weight.

50 ml of n-heptane is added to the reaction solution. The mixture is cooled to room temperature to give a white, finely crystalline precipitate, which is separated off. It consists of: 75% of 2,6-diisopropylnaphthalene dihydroperoxide, 9% of 2,6-diisopropylnaphthalene monohydroperoxide, and 16% of 2-(6-isopropyl)-naphth-2-yl-propan-2-ol and 2-(6-isopropyl)-naphthyl-methyl ketone.

The filtrate contains about 90% of 2,6-diisopropylnaphthalene and 2,6-diisopropylnaphthalene monohydroperoxide and about 1% of 2,6-diisopropylnaphthalene dihydroperoxide. The filtrate can be employed for a further autoxidation.

The crystalline precipitate is dissolved in 50 ml of methanol, and 1 ml of concentrated (37%) hydrochloric acid is added. The solution is then heated to 60° C. and left at this temperature for 15 minutes. The 2,6-dihydroxynaphthalene is then worked up and isolated as described in Example 1. Yield: 95%, relative to the 2,6-diisopropylnaphthalene dihydroperoxide obtained in the oxidation stage.

EXAMPLE 3

10 g of 2,6-diisopropylnaphthalene (98% content, according to GC), dissolved in 15 ml of an octane fraction (124°–128° C.) are heated to 110° C. in a 100 ml four-necked flask equipped with a stirrer, a thermometer, a reflux condenser and a gas inlet frit. After 0.1 ml of a solution composed of 4 parts of 2-ethylcaproic acid, 2 parts of sodium hydroxide and 5 parts of water has been added, 0.1 ml of ditertiary butyl peroxide is added to the reaction solution with vigorous stirring and oxygen is passed in at a rate of 65 ml/minute.

The reaction was terminated after 6 hours. Analysis of the reaction product by HPLC indicates, in addition to unchanged starting material, oxidation products consisting, to the extent of 82%, of 2,6-diisopropylnaphthalene monohydroxide and dihydroxide, the ratio by weight of these to one another being about 5:1.

When the reaction products are cooled to room temperature, reddish-white, 2,6-diisopropylnaphthalene dihydroperoxide crystallizes, together with a little 2,6-diisopropylnaphthalene monohydroperoxide. The latter can be largely extracted by washing with octane. The filtrate obtained on filtering off the mesh of crystals with suction can be re-employed in the oxidation reaction after 2,6-diisopropylnaphthalene has been added. The purified mash of crystals is taken up in methanol as described in Example 1 and is converted into 2,6-dihydroxynaphthalene by acid hydrolysis.

The yield of 2,6-dihydroxynaphthalene, relative to 2,6-diisopropylnaphthalene dihydroperoxide, is virtually quantitative.

2,6-Di-sec-butylnaphthalene can also be employed in the oxidation reaction with comparable results instead of 2,6-diisopropylnaphthalene.

What is claimed is:

1. A process for the preparation of 2,6-dihydroxynaphthalene, which comprises oxidizing 2,6-dialkylnaphthalenes, in an inert solvent, at temperatures from 50° to 150° C. by means of oxygen or oxygen donors in the presence of an alkali metal salt or alkaline earth metal salt of an organic carboxylic acid having 5 to 14 carbon atoms, to give the corresponding 2,6-dialkylnaphthalene dihydroperoxides, and then hydrolysing the latter under acid conditions.

2. A process according to claim 1, wherein the 2,6-dialkylnaphthalenes contain 2 to 4 carbon atoms in the alkyl moiety.

3. A process according to claim 2, wherein the 2,6-dialkylnaphthalenes are 2,6-di-sec-butylnaphthalenes or, 2,6-diisopropylnaphthalenes.

4. A process according to claim 1, wherein the alkali metal salts or alkaline earth metal salts of the organic carboxylic acids have the formula

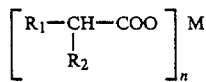

in which $R_1$ is $C_1-C_{12}$alkyl or naphthyl and $R_2$ is hydrogen or $C_1-C_9$alkyl, the sum of the carbon atoms in the substituents $R_1$ and $R_2$ is 3 to 12, M is lithium, sodium, or potassium, magnesium, strontium or calcium, and n is 1 or 2, depending on the valency of the metals M.

5. A process according to claim 1, wherein the alkali metal salts or alkaline earth metals salts of the organic carboxylic acids have the formula

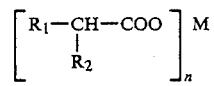

in which $R_1$ is $C_1-C_{12}$alkyl and $R_2$ is hydrogen or $C_1-C_9$alkyl, the sum of the carbon atoms in the substituents $R_1$ and $R_2$ is 3 to 12, M is lithium, sodium, potassium, magnesium, strontium or calcium, and n is 1 or 2, depending on the valency of the metals M.

6. A process according to claim 5, wherein the salts of n-valeric acid, caproic acid, n-heptanoic acid, caprylic acid, pelargonic acid, capric acid, lauric acid, myristic acid, 2-ethylbutyric acid, 4-ethylhexanoic acid, 3-ethylheptanoic acid or, 2-ethylcaproic acid are used.

7. A process according to claim 1, wherein the inert organic solvents are aromatic or aliphatic hydrocarbons having boiling points within the range from 60° to 150° C.

8. A process according to claim 1, wherein the oxidation is carried out in the presence of an additional reaction initiator which forms free radicals.

9. A process according to claim 8, wherein organic peroxide or azo compounds are used as reaction initiators.

10. A process according to claim 1, wherein the oxidation is carried out at temperatures from 70° to 130° C.

11. A process according to claim 10, wherein the oxidation is carried out at temperatures from 80° to 130° C.

12. A process according to claim 4, wherein the amount of the alkali metal salts or alkaline earth metal salts of the organic carboxylic acids is 0.1 to 0.5% by weight, relative to the 2,6-dialkyl-naphthalenes.

13. A process according to claim 2, wherein the 2,6-dialkylnaphthalene contain 3 or 4, carbon atoms in the alkyl moiety.

14. A process according to claim 5, wherein M is sodium or potassium.

15. A process according to claim 11, wherein the oxidation is carried out at temperatures from 80° to 110° C.

* * * * *